United States Patent
Langen et al.

(10) Patent No.: US 7,455,911 B2
(45) Date of Patent: Nov. 25, 2008

(54) ANTI-ADHESIVE COATING FOR TREATING BANDAGES

(75) Inventors: Günter Langen, Wolfstein (DE); Marita Meister, Kaiserslautern (DE); Horst Böttcher, Dresden (DE); Boris Mahltig, Dresden (DE)

(73) Assignee: Paul Hartman AG, Heidenheim (DE)

( * ) Notice: Subject to any disclaimer, the term of this patent is extended or adjusted under 35 U.S.C. 154(b) by 130 days.

(21) Appl. No.: 10/532,583

(22) PCT Filed: Oct. 24, 2003

(86) PCT No.: PCT/EP03/11819

§ 371 (c)(1),
(2), (4) Date: May 17, 2005

(87) PCT Pub. No.: WO2004/037139

PCT Pub. Date: May 6, 2004

(65) Prior Publication Data

US 2006/0014030 A1    Jan. 19, 2006

(30) Foreign Application Priority Data

Oct. 25, 2002    (DE) ................ 102 49 874

(51) Int. Cl.
*A61F 13/53*    (2006.01)
*B32B 9/04*    (2006.01)

(52) U.S. Cl. ............ 428/447; 602/42; 602/43; 602/52

(58) Field of Classification Search ........... 428/447; 602/42, 43, 52
See application file for complete search history.

(56) References Cited

U.S. PATENT DOCUMENTS

| 6,270,792 | B1 | 8/2001 | Guillemet et al. |
| 6,462,100 | B1 * | 10/2002 | Thunhorst et al. ............ 521/53 |
| 6,991,802 | B1 * | 1/2006 | Ahola et al. ................ 424/423 |
| 7,112,339 | B1 * | 9/2006 | Ahola et al. ................ 424/484 |
| 7,157,518 | B2 * | 1/2007 | Biteau et al. ................ 524/588 |
| 2003/0104039 | A1 | 6/2003 | Berthold et al. |
| 2004/0120971 | A1 * | 6/2004 | Koskinen et al. ......... 424/204.1 |
| 2004/0197414 | A1 * | 10/2004 | Ahola et al. ................ 424/489 |
| 2005/0084438 | A1 * | 4/2005 | Do et al. ................ 423/244.02 |

FOREIGN PATENT DOCUMENTS

| DE | 100 06 125 A1 | 8/2001 |
| DE | 100 14 557 A1 | 10/2001 |
| DE | 100 15 600 A1 | 10/2001 |
| DE | 100 54 119 A1 | 5/2002 |
| EP | 0 047 492 A2 | 3/1982 |
| EP | 0 261 167 B1 | 1/1992 |
| EP | 1 097 682 A2 | 5/2001 |
| EP | 1 106 149 A2 | 6/2001 |
| WO | WO 99/61077 A1 | 12/1999 |
| WO | WO 00/01425 A1 | 1/2000 |
| WO | WO 00/16725 A2 | 3/2000 |

* cited by examiner

*Primary Examiner*—Margaret G Moore
(74) *Attorney, Agent, or Firm*—Caesar, Rivise, Bernstein, Cohen & Pokotilow, Ltd.

(57) ABSTRACT

A coating composition is described for the anti-adhesive coating of wound dressings, comprising a nanosol that contains silica and at least one hydrophobic organic silicon compound, anti-adhesive layers prepared therefrom, coated wound dressings and methods for their manufacture.

13 Claims, No Drawings

ANTI-ADHESIVE COATING FOR TREATING BANDAGES

BACKGROUND OF THE INVENTION

The invention relates to coating compositions for the anti-adhesive coating of wound dressings, anti-adhesive layers, especially for wound dressings, anti-adhesive coated dressings and methods for manufacture of the coating compositions or anti-adhesive layers.

The purpose of a bandage is to protect the wound from the effects of its surroundings, to absorb the wound fluid and to aid in the healing process. It is known that during the healing process the wound and the bandaging material stick together. During changing of the wound padding, this sticking of wound to bandage can lead to renewed damage to the healing wound. In addition to the pain which a patient, especially one having chronic wounds, has to endure during regular bandage changing, repeated damage to the healing wound also results in an overall delay in the wound healing process. On this basis it is desirable that bandages have low tendency to stick to the wound.

Up until now, methods to produce bandages having low tendency to stick issue mostly from a multilayer bandage material comprising layers of different types of textile (WO99/611077; European Patent 1097682; German Patent 10014557). The textile layer which is immediately adjacent to the wound in these bandages usually consists of a hydrophobic textile or a polymer film, which has only a small tendency to stick to the wound. Behind this contact layer, an absorbent textile material is then applied for absorption of fluid from the wound. In contrast to wound dressings that consist of only one type of textile, such multilayer bandage systems have essentially two disadvantages. For one, they are less convenient to handle, since the wound may be covered exclusively by the contact area of the wound dressing. Another reason is that the manufacture of such multilayer wound dressings is significantly more costly in comparison to single component materials, since two different textile materials must be joined together in an additional operation.

In a new type of multilayer bandage material the surface, which is directly on top of the wound, consists of an elastomeric hydrogel layer, which can have hydrophilic as well as hydrophobic properties (WO00/16725; European Patent 261167). These systems do indeed have a significantly lower tendency to stick to the wound, but are difficult to handle, since firstly only the dressing contact itself may be placed on the wound and additional precautions must be taken so that the hydrogel is not dried out or contaminated. Another disadvantage is that the manufacture of such multilayer bandages with a hydrogel layer is significantly more expensive than the production of bandage systems consisting of only one textile material.

Based on the disadvantages of multilayer bandage systems methods were evolved to develop textile materials having low sticking tendencies and at the same time good water absorption capabilities. One method therein comprises interweaving hydrophobic and hydrophilic strands with each other resulting in a single layer textile wound dressing having lower wound adhesion (European Patent 1106149). Thus, a single layer bandage of a mixed web is provided. It is more favorable, however, if a conventional material is modified in such a manner that it exhibits decreased adhesion to the wound.

Such a method is presented by the hydrophobic modification of cellulose material by means of carboxylation (WO 00/01425). Making cellulose hydrophobic lowers the adhesion of wound dressings to the wound and thereby induces a decreased tendency to stick. However, the disadvantage of this method is that it only permits the modification of cellulose bandages whereas other bandage materials such as, for example, polyamide or viscose can not be improved by carboxylation.

The object of the invention is to provide improved coating compositions for the anti-adhesive preparation of wound dressings, with which the disadvantages of conventional wound dressings are avoided, and methods for their manufacture. In particular, the coating compositions should allow the production of wound dressings having decreased tendency for sticking between the wound and the bandage material. Moreover, the preparation of cost-effective anti-adhesive wound dressings should be made possible. Further, the invention should also be applicable to different bandage materials.

These objects are achieved by means of coating compositions, anti-adhesive layers, wound dressings and methods having the features as described herein.

SUMMARY OF THE INVENTION

A basic idea of the invention is especially to provide anti-adhesive coating compositions (coating means) for treating wound dressings based on layer-forming nanosols, which contain silica and at least one hydrophobic or oleophobic acting organic silicon compound (so-called Component A). This combination has the particular advantage that the capability for forming stable coatings, which adhere to the wound dressing, and the anti-adhesive action of the organic silicon compound are combined.

Anti-adhesive layers herein are coatings formed on the supporting bandage material (or wound dressing) and having an effect that lowers adherence of adjacent materials, especially of parts of the wound, substances emerging from the wound, or substances applied thereon.

DETAILED DESCRIPTION OF THE PREFERRED EMBODIMENTS

The wound dressing consists of a flat textile form, foamed plastic or a gel. For the flat textile form (textile material) different types of textiles (fabrics, wovens, knitted, non-woven-textiles) made from natural fibers (such as, e.g. cotton, viscose) or chemical fibers (such as e.g. polyamide, polyester, polypropylene, polyethylene, polyacrylonitrile, polyacetate, polyurethane, rubber, calcium alginate, chitosan or mixtures of these fibers) can be used. Foamed plastic wound dressings consist for instance of natural latex, synthetic latex or polyurethane. Gels as wound dressings consist for example of gelatin, alginate, polysaccharine, starch, starch ethers, starch esters, cellulose, cellulose ethers, cellulose esters, galactomannans or polyurethanes and contain, if necessary, super-absorptive additives (SOP) based on polyacrylate, starch derivatives or cellulose derivatives. The wound dressing preferably consists of a single layer material such as known from conventional bandages and which in addition to the decreased adhesion to the wound has a sufficient absorptive capacity, e.g. for wound secretion.

It is especially provided, for the coating of wound dressings, to use layer-forming nanosols, which are formed by hydrolysis of tetraalkoxysilanes and a hydrophobic and if necessary oleophobic acting organic silicon compound in organic, organic-aqueous or aqueous solvents. Thin anti-adhesive quasi-ceramic coatings are produced on a wound dressing by means of a sol gel method.

The liquid coating means for treating wound bandages comprises a hydrophobic modified silica-nanosol in organic, aqueous or mixed solvents. The nanosol particles are prepared by acid or alkaline catalyzed hydrolysis of a tetraalkoxysilane $Si(OR)_4$, wherein R preferably contains 1 to 4 carbon atoms:

$$Si(OR)_4 + 2H_2O \rightarrow (SiO_2)_n + 4ROH \qquad (1)$$

The $(SiO_2)_n$ formed is present in the aqueous solution in nanoparticle form. Depending on the reaction conditions the mean particle size is e.g. between 2 and 15 nm. The alcohol formed during the hydrolysis can be gently evaporated and substituted by water so that, if necessary, pure aqueous nanosols can be used as well. Due to the extreme ratio of particle surface area to particle volume a change of the surrounding conditions (neutralization of the solution, increase in temperature, increase in concentration) leads to rapid gelling ("sol gel process") of the nanosols. Therefore, it is possible to employ nanosols advantageously as coating means, wherein in the case of a coating and subsequent drying, first solvent-containing lyogel coatings are produced, which in the course of the drying process turn into dry stable xerogel coatings having a quasi-ceramic character.

$$(SiO_2)_{n,sol} \longrightarrow \text{lyogel} \longrightarrow \text{xerogel quasi-ceramic coating} \qquad (2)$$

The relative coating weight of the xerogel coatings on the wound dressing advantageously is between 0.05% and 5%, preferably 0.2 to 2%. For coated textiles, depending on the type of compound and tempering temperature, for instance coatings having an area density of 0.1 $g/m^2$ to 50 $g/m^2$ in relation to the area of coated textile are formed.

The coating can be formed advantageously as a homogeneous isotropic distribution in the whole wound dressing (e.g. by impregnating, immersion coating, foularding), single-sided coating as a thin layer on one surface of the wound dressing (e.g. by means of padding, rolling, spray coating, painting, especially squeegee rolling, floating knife), or as two-sided coating with thin layers on both surfaces of the wound dressing by simultaneously or consecutively implemented steps of an application process as in the single-sided coating. The coating can be formed as a closed layer or as a partly open layer, e.g. with a network or island-forming pattern. Such a patterned thin layer is produced for instance by means of a grid rolling application, pressure stencil or screen printing, wherein in each case the desired geometric pattern is realized with partial distribution of the nanosol on the surface of the wound dressing.

$SiO_2$ coatings coated on textile wound dressings with pure $SiO_2$ nanosols exhibit only small changes in adhesive behavior. The lowered sticking tendency of the coated wound dressing is, in accordance with the invention, obtained by means of the addition of the hydrophobic acting silicon-containing component A and, if necessary, co-hydrolysis thereof. The component A can be added before or after hydrolysis of tetraalkoxysilane according to equation (1), without significant changes in properties of the coating solutions.

For component A (organic silicon compound) may be used:

Trialkoxysilanes $R^1Si(OR)_3$, wherein $R^1$ is an alkyl group having 8 to 18 carbon atoms. Increasingly hydrophobic properties and decreased wound adhesion can be provided by employing alkyl groups with longer chain length.

Arylsilanes $R^2Si(OR)_3$ or diarylsilanes $R^2_2Si(OR)_2$, wherein $R^2$ is an aryl group, preferably a phenyl group. The phenyl group having 6 C atoms provides a hydrophobicity corresponding to that of an alkyl group of equal length.

Triphenylsilane chloride or t-butyldiphenylsilane chloride. These improve the hydrophobicity in comparison to the previously mentioned arylsilanes.

Polysiloxanes with methyl and/or phenyl side groups, which can be co-hydrolyzed by means of reactive chain ends. For reactive chain ends hydroxyl groups (a) or epoxy units (b) may be utilized.

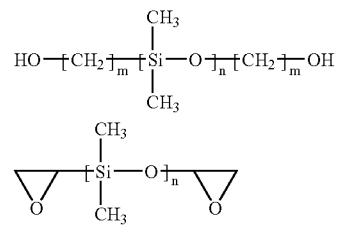

With increasing degree of polymerization of the polysiloxane an increased hydrophobicity of the textile wound dressings can be produced.

Alkyltrialkoxysilane compounds $R^3Si(OR)_3$ having a perfluorinated alkyl group $R^3$.

Polysiloxane compounds having perfluorinated alkyl side chains. By introducing fluorinated alkyl groups, hydrophobic as well also as oleophobic properties can be obtained on the coated wound dressings. The adhesion between the coated wound dressing and the wound is correspondingly reduced.

In addition to the introduction of alkyltrialkoxysilanes $R_1Si(OR)_3$ as hydrophobic additives to pure $SiO_2$ nanosols these alkylsilane compounds can also be hydrolyzed in alcohol with each other by themselves, that is without addition of TEOS, and be utilized as coating means.

Depending on the type of compound, the amount of A added amounts to between 1 and 50 wt % in relation to the total amount of solid material.

By the addition and co-hydrolysis of epoxysilanes, preferably 3-glycidyloxypropyltrialkoxysilanes, in amounts up to 50 wt %, to the tetraalkoxysilanes corresponding to equation (1), partially hydrophilic layer properties can be achieved. These properties together with a good anti-adhesive effect promote in an advantageous way high water absorption ability or water permeability of the textile body and thereby the absorption of wound secretion. Furthermore, the adhesion of the coating to the textile support is improved.

Generally, the use of hydrolysable, silicon-containing compounds as hydrophobic component A results in the strong association of the hydrophobic property with the textile layer, and therewith represents an important advantage compared to the use of pure components.

The anti-adhesive coatings can, in accordance with the invention, for that reason be utilized advantageously for the treating of wound dressings in order to decrease the adhesion between wound and wound dressing.

There are important advantages of the invention compared to the state of the art, as follows:

The adhesion between wound and wound dressing is lowered.

The coating means used allow conferring the non-sticking properties to conventional, especially single layer, textile wound dressings, whereas up until now most multi-layer dressings made up from different textile materials have been used.

By use of the coating means, the non-sticking properties can be similarly conferred to different textile types.

The additional supplement of hydrophilic components allows the manufacture of textile materials with a hydrophobic surface and decreased sticking tendency with the advantage at the same time of the textile substrate having fluid absorption capability.

EXAMPLES OF SPECIFIC EMBODIMENTS

1. Manufacture of the Nanosols

Sol 1: 4 ml of 0.01N HCl are added drop-wise to a mixture of 20 ml of tetraethoxysilane (TEOS) and 84 ml of ethanol and stirred for 20 hours at room temperature. A stable water-clear gel is obtained.

Sol 2: 12 ml of 0.01N HCl are added drop-wise to a mixture of 34 ml of TEOS, 4 ml of 3-glycidyloxypropyl-triethoxysilane (GLYEO) and 50 ml of ethanol and stirred for 20 hours at room temperature. A stable water-clear gel is obtained.

Sol 3: 5 ml of 0.01N HCl are added drop-wise to a mixture of 5 ml of TEOS, 5 ml of methyltriethoxysilane and 85 ml of EtOH and stirred for 20 hours at room temperature. A stable water-clear gel is obtained.

Sol 4: A mixture of 15 ml of methyltriethoxysilane and 15 ml of phenyltriethoxyilane in 90 ml ethanol and 5 ml of 0.01N HCl is stirred for 20 hours at room temperature.

Sol 5. 5 ml of 0.01N HCl are added drop-wise to a mixture of 20 ml methyltriethoxysilane and 85 ml of ethanol and stirred for 20 hours at room temperature.

2. Manufacture of the Coating Composition

The manufacture of the coating compound is carried out by mixing of the nanosols with hydrophobic acting components immediately before coating to a homogeneous sol. Furthermore, the coating compound can be further diluted with ethanol or water for the application.

Hydrophobic acting components A:
A1: isobutyltriethoxysilane (proportion of 3%)
A2: octyltriethoxysilane (proportion of 3%)
A3: hexadecyltrimethoxysilane (proportion of 3%)
A4: perfluorooctyltriethoxysilane (proportion of 1%)

3. Applications of the Coating Compositions

The coating compositions are utilized for coating textile wound dressings of cotton, viscose and viscose/polyester, as well as on glass for evaluation of the hydrophobic properties. The coatings are made by means of dip-coating (drawing speed 30 cm/min) or foularding (speed 3 m/min at pressures of 3-6 bar). After drying the coated substrates are thermally treated between 25° C. and 180° C. Evaluation of the hydrophobic properties is carried out by means of contact angle measurements on the coated materials. The wound adhesion of the coated materials is evaluated by means of separation force measurements on a protein solution with fibrinogen. The results of the separation force measurements for samples obtained by dip-coating are presented in the following table for a few application examples.

| Sol | Hydrophobic Component | Textile Material | Tempering Temperature [° C.] | Separation Force [N] |
|---|---|---|---|---|
| Uncoated Reference Textile | — | Viscose-Knitware | — | 0.40 |
| Uncoated Reference Textile | — | Cotton-Fabric | — | 0.89 |
| 1 | A2 | Viscose-Knitware | 120° C. | 0.34 |
| 2 | A1 | Viscose-Knitware | 120° C. | 0.12 |
| 2 | A2 | Viscose-Knitware | 120° C. | 0.18 |
| 2 | A3 | Viscose-Knitware | 120° C. | 0.14 |
| 3 | A4 | Cotton-Fabric | 60° C. | 0.44 |
| 3 | A4 | Viscose-Knitware | 60° C. | 0.15 |
| 4 | — | Cotton-Fabric | 60° C. | 0.59 |
| 5 | — | Cotton-Fabric | 60° C. | 0.33 |
| 5 | — | Viscose-Knitware | 60° C. | 0.25 |

4. Preferred Application Example

The textile material has a flat shape analogous to that in German Patent 3213673, in the form of a knitted wound fabric of 100% Viscose with an area weight of 236 g/m$^2$. The coating means is manufactured by mixing of sol 2 with 3 % hexaadecyltrimethoxysilane as hydrophobic component. The coating bath is a 5% dilution of the coating means in ethanol. The coating is carried out with a Foulard, consisting of two rolls arranged vertically and a chassis, at a speed of 3 m/min. The ambient pressure is 2 bar, such that a take up from the bath of 207 g/m$^2$ is achieved. Subsequently the coated material is hung in air for two hours to dry. The tempering is carried out while hanging in a heat chamber at 120° C. The coating weight amounts to 0.7 %. The separation force measurement gives a result of 0.29N.

The separation force measurements for evaluation of the wound adhesion of the coated materials are carried out with a standardized measurement method of the "Institutes for Physiology of Apparel in Hohenstein" (Bekleidungsphysiologischen Institute Hohenstein) (AW-QM-11.01/06/08.03.013). This measurement method is carried out with the following auxiliary means. For the test piece the coated (or impregnated) textile is used. A glass plate serves as a supporting material onto which a fibrinogen solution and the textile are placed. In order to prevent run-off of the fibrinogen solution when spread on the glass plate, tape is attached to the edge of the plate as a seal. Another strip of adhesive tape ("Tesa Moll") is fastened to the plate as an additional seal. The textile test piece is stitched to one of the narrow ends with an elastic plastic strip for the separation force measurements subsequently carried out.

For carrying out the separation force measurements, first the fibrinogen solution is applied to the horizontally arranged glass plate and distributed evenly. The test piece is laid on top of the fibrinogen solution without applying pressure. Surface drying of the test piece on the fibrinogen coating follows at room temperature for a period of 2 hours. After this time the test pieces are kept under normal ambient climate conditions. For determination of the separation force value a tensile test machine is utilized. For this the glass plate is held in the lower clamp jaws of the tensile test machine and the plastic strip is held in the upper clamp jaws. Subsequently, the test piece is separated from the fibrinogen layer. The force that is needed to separate the test piece from the fibrinogen layer is measured.

The invention claimed is:

1. A composite comprising:
   a wound dressing;
   an anti-adhesive layer comprising a xerogel with silica and at least one hydrophobic organic silicon compound, wherein the anti-adhesive layer has a relative coating weight on the wound dressing from 0.05% and 5%; and
   an epoxysilane compound effective to provide the anti-adhesive layer with partially hydrophilic properties.

2. The composite according to claim 1, wherein the at least one hydrophobic organic silicon compound comprises at least one compound selected from the group consisting of:
   a trialkoxysilane having the formula $R^1Si(OR)_3$, wherein $R^1$ is an alkyl group having 8 to 18 carbon atoms;
   an arylsilane having the formula $R^2Si(OR)_3$, wherein $R^2$ is an aryl group;
   a diarylsilane having the formula $R^2_2Si(OR)_2$, wherein $R^2$ is an aryl group;
   triphenylsilane chloride;
   t-butyldiphenylsilane chloride;
   hydrophobically modified polysiloxanes having alkyl and/or phenyl side groups;
   oleophobic compounds having the formula $R^3Si(OR)_3$, wherein $R^3$ is a perfluorinated alkyl group; and
   oleophobic polysiloxanes having perfluorinated alkyl side chains.

3. The composite according to claim 1, wherein the wound dressing comprises a flat textile form, a foamed plastic or a gel.

4. The composite according to claim 1, wherein the anti-adhesive layer consists essentially of the xerogel with silica, the epoxysilane compound and the at least one hydrophobic organic silicon compound.

5. The composite according to claim 1, wherein the at least one hydrophobic organic silicon compound comprises at least one compound selected from the group consisting of:
   an arylsilane having the formula $R^2Si(OR)_3$, wherein $R^2$ an aryl group;
   a diarylsilane having the formula $R^2_2Si(OR)_2$, wherein $R^2$ is an aryl group;
   triphenylsilane chloride;
   t-butyldiphenylsilane chloride;
   hydrophobically modified polysiloxanes having alkyl and/or phenyl side groups;
   oleophobic compounds having the formula $R^3Si(OR)_3$, wherein $R^3$ is a perfluorinated alkyl group; and
   oleophobic polysiloxanes having perfluorinated alkyl side chains.

6. A method for preparing the composite of claim 1, said method comprising:
   hydrolyzing tetraalkoxysilanes in an organic, organic-aqueous or aqueous solvent to provide a nanosol,
   mixing the at least one hydrophobic organic silicon compound and an epoxysilane compound with the nanosol to prepare a coating composition and
   applying the coating composition on the wound dressing and drying the coating composition on the wound dressing by solvent removal to form a xerogel layer on the wound dressing.

7. The method according claim 6, wherein the step of applying the coating composition comprises a single-sided coating, a two-sided coating or an impregnation of the wound dressing.

8. The method according to claim 6, wherein the step of applying the coating is implemented as a closed coating or impregnation or as a partly discontinuous coating or impregnation.

9. The method according to claim 6, further comprising a heat treatment step conducted at a temperature from 25° C. to 180° C. following the drying step.

10. The method according to claim 6, wherein the anti-adhesive coating decreases adhesion between a wound and the wound dressing.

11. The method according to claim 6, wherein the at least one hydrophobic organic silicon compound comprises at least one compound selected from the group consisting of:
    a trialkoxysilane having the formula $R^1Si(OR)_3$, wherein $R^1$ is an alkyl group having 8 to 18 carbon atoms;
    an arylsilane having the formula $R^2Si(OR)_3$, wherein $R^2$ is an aryl group;
    a diarylsilane having the formula $R^2_2Si(OR)_2$, wherein $R^2$ is an aryl group;
    triphenylsilane chloride;
    t-butyldiphenylsilane chloride;
    hydrophobically modified polysiloxanes having alkyl and/or phenyl side groups;
    oleophobic compounds having the formula $R^3Si(OR)_3$, wherein $R^3$ is a perfluorinated alkyl group; and
    oleophobic polysiloxanes having perfluorinated alkyl side chains.

12. A composite comprising:
    a wound dressing; and
    an anti-adhesive layer comprising a xerogel with silica and at least one hydrophobic organic silicon compound selected from the group consisting of:
    a trialkoxysilane having the formula $R^1Si(OR)_3$, wherein $R^1$ is an alkyl group having 8 to 18 carbon atoms;
    an arylsilane having the formula $R^2Si(OR)_3$, wherein $R^2$ is an aryl group;
    a diarylsilane having the formula $R^2_2Si(OR)_2$, wherein $R^2$ is an aryl group;
    triphenylsilane chloride;
    t-butyldiphenylsilane chloride;
    hydrophobically modified polysiloxanes having phenyl side groups;
    oleophobic compounds having the formula $R^3Si(OR)_3$, wherein $R^3$ is a perfluorinated alkyl group; and
    oleophobic polysiloxanes having perfluorinated alkyl side chains,
    wherein the anti-adhesive layer has a relative coating weight on the wound dressing from 0.05% to 5%.

13. A composite comprising:
    a wound dressing; and
    an anti-adhesive layer comprising a xerogel with silica and at least one hydrophobic organic silicon compound selected from the group consisting of:
    an arylsilane having the formula $R^2Si(OR)_3$, wherein $R^2$ is an aryl group;
    a diarylsilane having the formula $R^2_2Si(OR)_2$, wherein $R^2$ is an aryl group;
    triphenylsilane chloride;
    t-butyldiphenylsilane chloride;
    hydrophobically modified polysiloxanes having phenyl side groups;
    oleophobic compounds having the formula $R^3Si(OR)_3$, wherein $R^3$ is a perfluorinated alkyl group; and
    oleophobic polysiloxanes having perfluorinated alkyl side chains,
    wherein the anti-adhesive layer has a relative coating weight on the wound dressing from 0.05% to 5%.

* * * * *